(12) United States Patent
Chen et al.

(10) Patent No.: US 7,981,630 B2
(45) Date of Patent: Jul. 19, 2011

(54) CBARA1 AND LHX6 CELL MARKERS FOR EMBRYONIC STEM CELLS

(75) Inventors: Chen-Ming Chen, Nantou County (TW); Wann-Hsin Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/483,434

(22) Filed: Jun. 12, 2009

(65) Prior Publication Data

US 2010/0316997 A1     Dec. 16, 2010

(51) Int. Cl.
*G01N 33/567*     (2006.01)
*C12N 5/00*     (2006.01)

(52) U.S. Cl. .......................... 435/7.21; 435/373; 435/383

(58) Field of Classification Search .................... None
See application file for complete search history.

(56) References Cited

PUBLICATIONS

Riekstina et al. Embryonic Stem Cell Marker Expression Pattern in Human Mesenchymal Stem Cells Derived from Bone Marrow, Adipose Tissue, Heart and Dermis. Stem Cell REviews and Reports, 2009, vol. 9, pp. 378-386.*

\* cited by examiner

*Primary Examiner* — Deborah Crouch
(74) *Attorney, Agent, or Firm* — Thomas, Kayden, Horstemeyer & Risley, LLP

(57) ABSTRACT

Polynucleotides associated with differentiation states of stem cells are provided. Also provided are methods and kits for detecting, identifying and/or discriminating differentiated stem cells from undifferentiated ones by measuring an expression level of one or more genes, such as CBARA1 and LHX 6, in the stem cells.

16 Claims, 5 Drawing Sheets
(2 of 5 Drawing Sheet(s) Filed in Color)

SEQUENCE LISTING

<160> NUMBER OF SEQ ID NOS: 4

<210> SEQ ID NO 1
<211> LENGTH: 2425
<212> TYPE: DNA
<213> ORGANISM: Homo sapiens

<400> SEQUENCE: 1

```
aggcccagcg gctaggagag tcacgtgaga gtgggcggag ggggtggagg tttgtctccg      60
ctgtttcatc tctatggctg tcagaggtgg gcggctttga ccgagaggct gctggagctc     120
gtgtttggac gcgatgtttc gtctgaactc actttctgct ttggcagaac tggctgtggg     180
ttctcgatgg taccatggag gatcacagcc catccagatc cggcgaagac taatgatggt     240
ggctttcctg ggagcatctg cagtaactgc aagtactggt cttttgtgga agagggccca     300
tgcagaatct ccaccatgtg tagacaacct aaaaagtgac atcggtgata aagggaagaa     360
taaagatgaa ggggatgttt gtaaccatga gaaaagact gcagatcttg cccctcaccc     420
agaagagaaa aagaagaaac gttctggatt cagagacaga aaagtgatgg aatatgagaa     480
taggattcga gcctactcca cgccagacaa aatcttccga tattttgcca ccttgaaagt     540
catcagtgag cctggtgaag cagaagtgtt tatgacacca gaagattttg tgcgatccat     600
aacacccaat gaaaaacaac cagaacactt gggtctggat caatatataa taaaacgctt     660
tgatggaaag acagagaaaa tttcccagga acgagaaaaa tttgctgatg aaggcagtat     720 atttttacacc cttggagaat gtgggctcat atccttttca gactacattt tcctcacaac     780
tgttctttcc actcctcaga gaaattttga aattgccttc aagatgtttg atttgaatgg     840
agatggagaa gtagatatgg aagaatttga acaggttcag agcatcattc gctcccaaac     900
cagtatgggt atgcgccaca gagatcgtcc aactactggc aacaccctca gtctggctt     960 gtgttcagcc ctcacaacct actttttggg agctgatctg aagggaaagc tgacaatcaa    1020
aaacttcctc gaatttcagc gtaaactgca gcatgatgtt ctgaagcttg agtttgaacg    1080 ccatgacct gtggatggga gaattactga gaggcagttt ggtggcatgc tacttgccta    1140
cagtggggtg cagtccaaga agctgaccgc catgcagagg cagctcaaga agcacttcaa    1200
agaaggaaag ggtctgacat tcaggaggt ggagaacttc tttactttcc taagaacat    1260 taatgatgtg gacactgcat tgagttttta ccatatggct ggagcatctc ttgataaagt    1320
gaccatgcag caggtggcca ggacagtggc taaagtggag ctctcagacc acgtgtgtga    1380
tgtggtgttt gcactctttg actgtgatgg caatggcgaa ctgagcaata aggaatttgt    1440
ttccatcatg aagcaacggc tgatgagagg cctggaaaag cccaaagaca tgggtttcac    1500
tcgcctcatg caggccatgt ggaaatgtgc acaggaaact gcctgggact tcgctttacc    1560
caaacagtaa ccccacactg caagagggga cccctccacc cccagtaccc tggaccccct    1620
ccgcagagtc tcggcagagc cctttgtgct gctgcttctg gaagtagtcc cccttcctcc    1680
cgggatgacc tcaggactct gtcggttttcc cctctttacc cttcccgtc cccgtgttct    1740 gctgggctct gattctgccc aatgagtatc cccataggtt ctcaaaaaca tgaacaagtc    1800
```

| | |
|---|---|
| tgtaaagctc agacatttgt cagcctcaac agcaccaccc attcaagcat cctgtggata | 1860 |
| aagaattcag ggaccatcc acacacctgc caaccctggg aagcatccag ttctcaaatc | 1920 |
| gtttttgcta tggatttata ctaacaagaa cattccttga cttccctcct gctggtgttt | 1980 |
| taaagccaca agtagggaag atatctggca ggcagaaaga agtctgtgat gataaacaat | 2040 |
| gatgaggatg acctaggcac cctacgctag tgtgagaagc ctgcgcccca ggaaggatct | 2100 |
| gtgttagtcc ctgggatggc tccaaggcct gctctaggaa ggcagcatgc tcagtgggaa | 2160 |
| cacagcaaga ttcagaattt aaagtagttg cttcatggct ctgtgcactc ccttttcttc | 2220 |
| ctcgcagcct ccctaagatg actccagtgt gaccctgtgc ttagtgagca atagtgattg | 2280 |
| agctcatgtt ccctgcaagt gccatttcct ctccaggatg ggcctctaaa gctgaggcct | 2340 |
| ggctcagagc ctgtttgccc tctgtcttaa acaattgtaa atatcactta aattataacc | 2400 |
| atttgcaata acatccccca aagtt | 2425 |

<210> SEQ ID NO 2
<211> LENGTH: 3377
<212> TYPE: DNA
<213> ORGANISM: Homo sapiens

<400> SEQUENCE: 2

| | |
|---|---|
| atgtactgga agcatgagaa cgccgccccg gcgttgcccg agggctgccg gctgccggcc | 60 |
| gagggcggcc ccgccaccga ccaggtgatg gcccagccag ggtccggctg caaagcgacc | 120 |
| acccgctgtc ttgaagggac cgccgccgcc gccatggctc agtctgacgc cgaggccctg | 180 |
| gcaggagctc tggacaagga cgagggtcag gcctccccat gtacgccag cacgccatct | 240 |
| gtctgctcac cgccctctgc cgcctcctcc gtgccgtctg caggcaagaa catctgctcc | 300 |
| agctgcggcc tcgagatcct ggaccgatat ctgctcaagg tcaacaacct catctggcac | 360 |
| gtgcggtgcc tcgagtgctc cgtgtgtcgc acgtcgctga gcagcagaa cagctgctac | 420 |
| atcaagaaca aggagatctt ctgcaagatg gactacttca gccgattcgg gaccaagtgt | 480 |
| gcccggtgcg ccgacagat ctacgccagc gactgggtgc ggagagctcg cggcaacgcc | 540 |
| taccacctgg cctgcttcgc ctgcttctcg tgcaagcgcc agctgtccac tggtgaggag | 600 |
| ttcggcctgg tcgaggagaa ggtgctctgc cgcatccact acgacaccat gattgagaac | 660 |
| ctcaagaggg ccgccgagaa cgggaacggc ctcacgttgg agggggcagt gccctcggaa | 720 |
| caggacagtc aacccaagcc ggccaagcgc gcgcggacgt ccttcaccgc ggaacagctg | 780 |
| caggttatgc aggcgcagtt cgcgcaggac aacaaccccg acgctcagac gctgcagaag | 840 |
| ctggcggaca tgacgggcct cagccggaga gtcatccagg tgtggtttca aaactgccgg | 900 |
| gcgcgtcata aaaagcacac gccgcaacac ccagtgccgc cctcggggc gccccgtcc | 960 |
| cgccttccct ccgccctgtc cgacgacatc cactacaccc cgttcagcag cccgagcgg | 1020 |
| gcgcgcatgg tcaccctgca cggctacatt gagagtcagg tacagtgcgg gcaggtgcac | 1080 |
| tgccggctgc cttacaccgc acccccgtc cacctcaaag ccgatatgga tgggccgctc | 1140 |
| tccaaccggg gtgagaaggt catccttttt cagtactaac gctgccggca ttccgcatc | 1200 |
| tgcccgtggg cgccccacag ctgcccctca gccgctgaga tccagtgtcc aagctgcggc | 1260 |
| caggagtcca cccacctccg catccacccc cgtccgccat cctgcccacc accaggtcgg | 1320 |
| ttcccgaggc ctggccttc cctctcctgc tgagaaccag aacccaccag gagcaccaca | 1380 |
| gagtcctcct cttggaaggc agaactccct gaaatctgga atcagggtgg aaacagcctg | 1440 |
| ttttcccat ttaaacagga gtcctcttca acttcagctg attacaataa caaaggcgg | 1500 |

```
aattgaattg tgcgatgcca acggccttct catttacagg ttttttttccc ccacattggc      1560 ctttatttac tacttccttg gaaccatctc tgaattctga atagctgaca accccccaatg     1620 ttatccactc tgttgctttt gtctggaaaa ctctacagtg tttgtgggat gtccccaaag      1680
gaaagctatg ttctaatttt atcatttcca tctgtctggt tatgtcaagt taattcagaa      1740
agagaagaga cagtgaccaa ccctgagagg cctaataggg cagagatgga ggcctgccca      1800
gactaggagg cagcggggat agacagggaa tggggagaag aaagaccccc attggtttgg      1860
aaatcaagga gagggcggtg acatattgga ccagaagagg cactagccat tttaaggaga      1920
ggaaagagaa aactctgggg tcagggagag accctacccc cacctaatta ccagcatat       1980 atgtaagaaa catagcagcg atggtattcg atctgtgcca tgactcttct gaatgtttgg      2040
acaggttaga gttggggacc cctgttggcc acttgttgac ctctcatagt ggtgcttggg      2100
ccaggtcttc tcaatggaag gggaatccct tataggggag agggaacaga gcccagtgaa      2160
atggcagtca gaatgttaac cctggatcca tctctaagta gagagagggt gcccattgcc      2220
taggtgagtg tgccaagctc aggattccaa ctggtgcctc tgagcttccc aatcaatact      2280
tcctggagcc agccccaccc accccctgaga acagaggtca gacacagctg cgtaacatcc     2340
atcctgctac aactcttcca ccccaaacaa aagggctcag gctacacacg accatgattt      2400
atgttttcag gggatgccca tttgtcccaa gcttatcctg taattctaga attacctggt      2460
gtcctgatgc attttccact agaggttgct aatcagcatg ttttagccca gtccgccttt     2520
cctgctgtgg ttaacctgtt atgttgcttt tggaaggaga ctctaagaca gggaaagcaa      2580
gttcatggta catacgcagc cattgtctct gttttttaccc atggcagaca ttgctaatca     2640
atggcagctc tatttcactg agtctggata aggtttcaga gttcaaatgc ttgacgttgg      2700
cacttaacat gaaagcctat aggtcattct tgctctggga tctacaggca gggtaggcac      2760
aggtgcagcc taagaaggga acctgcttcc tctcccttcc aaagacagtg acagctgact      2820
gagggcaaag agcaggcacc actcagaacg tggtgagtac agctcagctc agcactcagt      2880
cagtggtaac ttgtgcccag ccctgtgcta ggcgctgaca ttaacaggag caaccagggc      2940
ccaattcctg gccttggagc tcaaatcttt cctttgattt ttgctcctga tcatcaaggc      3000
cccagtggca accatgtggt aagtggccaa ccaagcccta cccagggtca cccaacacac      3060
tctgccttga gcctctcctc agggtctatt ccttgcgtgg attatgtggc cgtagcatgt      3120
tacagttcaa acatgtctcc actaccctgt taagagcagc ctgggaacgt acaggccatc      3180
aagactattt atttaaatac aaaaaaaggg gaaaacacac acacggaaaa aaaattgtaa      3240 gcacttttttt tgtaaaacca atgtctgttt tgttacatac cttttcatgtc gtgctttgta    3300 aatgtcttat ttgtgtaata aagttaatgc aagtagaagt gctggcactg aaatccagaa      3360
aaaaaaaaaa aaaaaaa                                                     3377

<210> SEQ ID NO 3
<211> LENGTH: 478
<212> TYPE: PRT
<213> ORGANISM: Homo sapiens

<400> SEQUENCE: 3

Met Phe Arg Leu Asn Ser Leu Ser Ala Leu Ala Glu Leu Ala Val Gly
1               5                   10                  15

Ser Arg Trp Tyr His Gly Gly Ser Gln Pro Ile Gln Ile Arg Arg Arg
            20                  25                  30

Leu Met Val Ala Phe Leu Gly Ala Ser Ala Val Thr Ala Ser Thr
        35                  40                  45
```

```
Gly Leu Leu Trp Lys Arg Ala His Ala Glu Ser Pro Pro Cys Val Asp
     50                  55                  60

Asn Leu Lys Ser Asp Ile Gly Asp Lys Gly Lys Asn Lys Asp Glu Gly
 65                  70                  75                  80

Asp Val Cys Asn His Glu Lys Lys Thr Ala Asp Leu Ala Pro His Pro
                 85                  90                  95

Glu Glu Lys Lys Lys Lys Arg Ser Gly Phe Arg Asp Arg Lys Val Met
            100                 105                 110

Glu Tyr Glu Asn Arg Ile Arg Ala Tyr Ser Thr Pro Asp Lys Ile Phe
            115                 120                 125

Arg Tyr Phe Ala Thr Leu Lys Val Ile Ser Glu Pro Gly Glu Ala Glu
130                 135                 140

Val Phe Met Thr Pro Glu Asp Phe Val Arg Ser Ile Thr Pro Asn Glu
145                 150                 155                 160

Lys Gln Pro Glu His Leu Gly Leu Asp Gln Tyr Ile Ile Lys Arg Phe
                165                 170                 175

Asp Gly Lys Thr Glu Lys Ile Ser Gln Glu Arg Glu Lys Phe Ala Asp
            180                 185                 190

Glu Gly Ser Ile Phe Tyr Thr Leu Gly Glu Cys Gly Leu Ile Ser Phe
            195                 200                 205

Ser Asp Tyr Ile Phe Leu Thr Thr Val Leu Ser Thr Pro Gln Arg Asn
210                 215                 220

Phe Glu Ile Ala Phe Lys Met Phe Asp Leu Asn Gly Asp Gly Glu Val
225                 230                 235                 240

Asp Met Glu Glu Phe Glu Gln Val Gln Ser Ile Ile Arg Ser Gln Thr
                245                 250                 255

Ser Met Gly Met Arg His Arg Asp Arg Pro Thr Thr Gly Asn Thr Leu
            260                 265                 270

Lys Ser Gly Leu Cys Ser Ala Leu Thr Thr Tyr Phe Phe Gly Ala Asp
            275                 280                 285

Leu Lys Gly Lys Leu Thr Ile Lys Asn Phe Leu Glu Phe Gln Arg Lys
290                 295                 300

Leu Gln His Asp Val Leu Lys Leu Glu Phe Glu Arg His Asp Pro Val
305                 310                 315                 320

Asp Gly Arg Ile Thr Glu Arg Gln Phe Gly Gly Met Leu Leu Ala Tyr
                325                 330                 335

Ser Gly Val Gln Ser Lys Lys Leu Thr Ala Met Gln Arg Gln Leu Lys
            340                 345                 350

Lys His Phe Lys Glu Gly Lys Gly Leu Thr Phe Gln Glu Val Glu Asn
            355                 360                 365

Phe Phe Thr Phe Leu Lys Asn Ile Asn Asp Val Asp Thr Ala Leu Ser
370                 375                 380

Phe Tyr His Met Ala Gly Ala Ser Leu Asp Lys Val Thr Met Gln Gln
385                 390                 395                 400

Val Ala Arg Thr Val Ala Lys Val Glu Leu Ser Asp His Val Cys Asp
                405                 410                 415

Val Val Phe Ala Leu Phe Asp Cys Asp Gly Asn Gly Glu Leu Ser Asn
            420                 425                 430

Lys Glu Phe Val Ser Ile Met Lys Gln Arg Leu Met Arg Gly Leu Glu
            435                 440                 445

Lys Pro Lys Asp Met Gly Phe Thr Arg Leu Met Gln Ala Met Trp Lys
450                 455                 460

Cys Ala Gln Glu Thr Ala Trp Asp Phe Ala Leu Pro Lys Gln
```

```
                465              470             475
```

<210> SEQ ID NO 4
<211> LENGTH: 392
<212> TYPE: PRT
<213> ORGANISM: Homo sapiens

<400> SEQUENCE: 4

```
Met Tyr Trp Lys His Glu Asn Ala Ala Pro Ala Leu Pro Glu Gly Cys
1               5                   10                  15

Arg Leu Pro Ala Glu Gly Gly Pro Ala Thr Asp Gln Val Met Ala Gln
            20                  25                  30

Pro Gly Ser Gly Cys Lys Ala Thr Thr Arg Cys Leu Glu Gly Thr Ala
        35                  40                  45

Pro Pro Ala Met Ala Gln Ser Asp Ala Glu Ala Leu Ala Gly Ala Leu
    50                  55                  60

Asp Lys Asp Glu Gly Gln Ala Ser Pro Cys Thr Pro Ser Thr Pro Ser
65                  70                  75                  80

Val Cys Ser Pro Pro Ser Ala Ala Ser Ser Val Pro Ser Ala Gly Lys
                85                  90                  95

Asn Ile Cys Ser Ser Cys Gly Leu Glu Ile Leu Asp Arg Tyr Leu Leu
            100                 105                 110

Lys Val Asn Asn Leu Ile Trp His Val Arg Cys Leu Glu Cys Ser Val
        115                 120                 125

Cys Arg Thr Ser Leu Arg Gln Gln Asn Ser Cys Tyr Ile Lys Asn Lys
    130                 135                 140

Glu Ile Phe Cys Lys Met Asp Tyr Phe Ser Arg Phe Gly Thr Lys Cys
145                 150                 155                 160

Ala Arg Cys Gly Arg Gln Ile Tyr Ala Ser Asp Trp Val Arg Arg Ala
                165                 170                 175

Arg Gly Asn Ala Tyr His Leu Ala Cys Phe Ala Cys Phe Ser Cys Lys
            180                 185                 190

Arg Gln Leu Ser Thr Gly Glu Glu Phe Gly Leu Val Glu Glu Lys Val
        195                 200                 205

Leu Cys Arg Ile His Tyr Asp Thr Met Ile Glu Asn Leu Lys Arg Ala
    210                 215                 220

Ala Glu Asn Gly Asn Gly Leu Thr Leu Glu Gly Ala Val Pro Ser Glu
225                 230                 235                 240

Gln Asp Ser Gln Pro Lys Pro Ala Lys Arg Ala Arg Thr Ser Phe Thr
                245                 250                 255

Ala Glu Gln Leu Gln Val Met Gln Ala Gln Phe Ala Gln Asp Asn Asn
            260                 265                 270

Pro Asp Ala Gln Thr Leu Gln Lys Leu Ala Asp Met Thr Gly Leu Ser
        275                 280                 285

Arg Arg Val Ile Gln Val Trp Phe Gln Asn Cys Arg Ala Arg His Lys
    290                 295                 300

Lys His Thr Pro Gln His Pro Val Pro Pro Ser Gly Ala Pro Pro Ser
305                 310                 315                 320

Arg Leu Pro Ser Ala Leu Ser Asp Asp Ile His Tyr Thr Pro Phe Ser
                325                 330                 335

Ser Pro Glu Arg Ala Arg Met Val Thr Leu His Gly Tyr Ile Glu Ser
            340                 345                 350

Gln Val Gln Cys Gly Gln Val His Cys Arg Leu Pro Tyr Thr Ala Pro
        355                 360                 365
```

-continued

```
Pro Val His Leu Lys Ala Asp Met Asp Gly Pro Leu Ser Asn Arg Gly
    370                 375                 380

Glu Lys Val Ile Leu Phe Gln Tyr
385                 390
```

US 7,981,630 B2

CBARA1 AND LHX6 CELL MARKERS FOR EMBRYONIC STEM CELLS

BACKGROUND

1. Technical Field

The disclosure in general relates to the discrimination of differentiated human embryonic stem cells (hESCs) from undifferentiated ones.

2. Description of Related Art

Stem cells have gained considerable interest as a treatment for a myriad of diseases, conditions, and disabilities because they are cells that have extensive proliferative capacity, and are capable of generating one or more kinds of progeny cells, or are capable of self-renewal or self-maintenance. However, spontaneous differentiation often occurs in stem cell cultures, resulting heterogeneous subsets of cells with reduced proliferative or developmental potential. Therefore, there exists in this art a need of an improved method for early discriminating differentiated stem cells from undifferentiated ones in stem cell cultures when spontaneous differentiation occurs.

SUMMARY

The disclosure relates to methods and kits for early detection of differentiated hESCs. Also, the disclosure provides novel stem cell markers, CBARA1 and LHX6, useful for discriminating differentiated hESCs from undifferentiated hESCs.

In a first aspect of the disclosure, there provides a method of discriminating differentiated human embryonic stem cells (hESCs) from undifferentiated hESCs, comprising the steps of: obtaining a population of hESCs; measuring an expression level of one or more polynucleotides comprising a nucleotide sequence at least 90% identical to any of SEQ ID NO 1 and SEQ ID NO 2 in the hESCs; and determining whether the expression level of the one or more polynucleotides in the hESCs is at least two folds lower than the expression level of the one or more polynucleotides in the undifferentiated hESCs. In particular embodiments, the expression level of the one or more polynucleotides is determined by measuring the level of one or more polypeptides encoded by the one or more polynucleotides. The one or more polypeptides comprise amino acid sequences at least 80% identical to any of SEQ ID NO: 3 and SEQ ID NO: 4.

In a second aspect, the disclosure provides a method of enriching a population of undifferentiated hESCs comprising the step of sorting hESCs by one or more cell markers selected from the group consisting of CBARA1 and LHX6. In one example, the cell marker is one or more genes having a nucleotide sequence at least 90% identical to any of SEQ ID NO 1 and SEQ ID NO 2; or one or more proteins encoded by the one or more gene, and the one or more proteins comprise amino acid sequences at least 80% identical to any of SEQ ID NO: 3 and SEQ ID NO: 4 In one example, the sorting is achieved by the use of flow cytometry. Similarly, in another example, the disclosure provides a method of removing differentiated hESCs from a population of hESCs, comprising the steps of: obtaining a population of hESCs; detecting the presence of at least one of CBARA1 and LHX6; and selecting out hESCs that are identified with a decrease in the at least one of CBARA1 and LHX6 for at least two folds.

In a third aspect, the disclosure provides a kit for use in early detecting or discriminating differentiated hESCs from undifferentiated hESCs, comprising one or more antibodies that recognize one or more proteins encoded by one or more polynucleotides having a nucleotide sequence at least 90% identical to any of SEQ ID NO 1 and 2; wherein the one or more proteins comprise a amino acid sequences at least 85% identical to any of SEQ ID NO 3 and 4 or a partial portion thereof. Alternatively, the kit may comprise a probe having a nucleotide sequence that is complementary to mRNA of a gene having a nucleotide sequence that is at least 90% identical to any of SEQ ID NO 1 and 2.

The disclosure thus provides the relevant art with a number of polynucleotides and polypeptides, which can be used as markers for early discriminating differentiated hESCs form undifferentiated hESCs, for example, as early as day 3 after differentiation occurs.

These and other features, aspects, and advantages of the present invention will become better understood with reference to the following description and appended claims.

It is to be understood that both the foregoing general description and the following detailed description are by examples, and are intended to provide further explanation of the invention as claimed.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The accompanying drawings are included to provide a further understanding of the invention, and are incorporated in and constitute a part of this specification. The drawings illustrate embodiments of the invention and, together with the description, serve to explain the principles of the invention. In the drawings.

DETAIL DESCRIPTION

Definition

Figure 1:
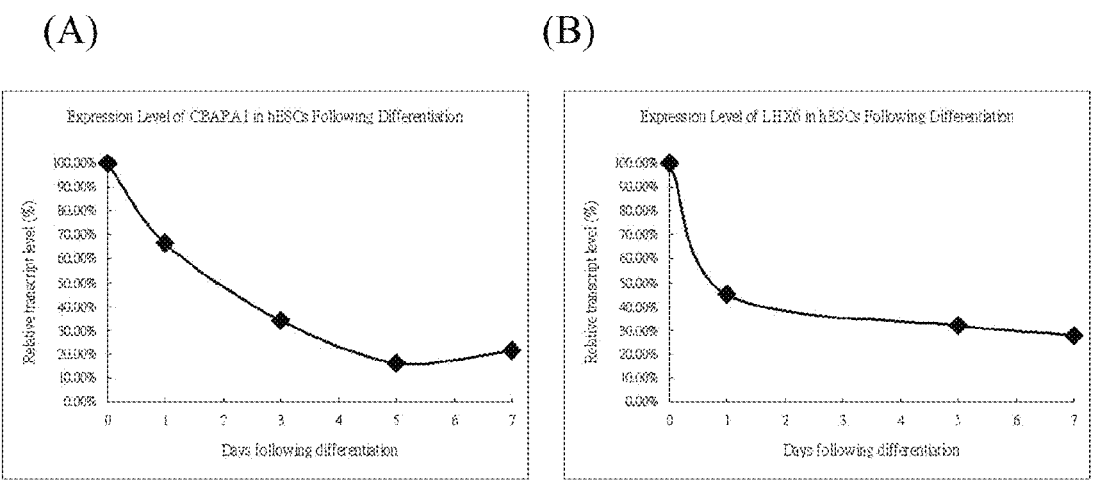
FIG. 1 illustrates the relative transcript level of (A) CBARA1 and (B) LHX6 decrease during differentiation.

As used herein, the terms "detecting", "identifying" and "discriminating" may be used interchangeably. By comparing the expression of one or more genes in a population of hESCs, one may determine whether a sub-population of hESCs is differentiated or not. If the level of the expressed gene product(s) in the selected population of hESCs is at least 2-folds lower than the normal undifferentiated cells, differentiated cells are "detected" or "identified"; or the selected population of hESCs is "discriminated" from the rest of hESCs.

As used herein, "cell marker" refers to a gene or genes or a protein, polypeptide, or peptide expressed by the gene or genes whose expression level, alone or in combination with other genes, is correlated with differentiation level of hESCs compared to undifferentiated cells.

As used herein, the terms "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells, or by chemical synthesis). Polypeptides according to the instant invention may also contain non-natural amino acids, as will be described below. The terms "polypeptide", "peptide" and "protein" are also used, in the instant specification, to designate a series of residues, typically L-amino acids, connected one to the other, typically by peptide bonds between the α-amino and carboxyl groups of adjacent amino acids.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

Description of Disclosure

The disclosure relates to the identification of novel genes that are expressed early, for example, as early as day 3 after spontaneous differentiation of hESCs occurs; and applications of the identified genes as markers for detecting, identifying and/or discriminating differentiated hESCs from non-differentiated hESCs.

The current development of stem cell therapeutics require early discrimination of differentiated hESCs from undifferentiated ones, hence useful cell markers for that purpose may greatly benefit the development of such medicaments.

The disclosure addresses this issue by providing markers for early detection or identification of differentiated hESCs, and thereby offering many advantages through the use of these markers. For example, differentiated hESCs may be identified as early as day 3 after spontaneous differentiation occurs. Also, the techniques provided by the disclosure for detecting, isolating or discriminating the differentiated hESCs from the undifferentiated ones are easy to use and are highly reproducible. The identified markers are fast-down regulated along the differentiation time course, when compared with the known hESC markers such as Oct4, Nanog, SSEA3, SSEA4, TRA-1-60 and TRA-1-81, which are not as sensitive as markers provided herein and are slowly down-regulated through out the entire differentiation course.

Work conducted during the development of the disclosure has shown that CBARA1 and LHX6 are useful markers for sorting out differentiated hESCs from a population of hESCs, with the expression of CBARA1 and LHX6 being fast down-regulated for about 30% and 50%, respectively at day 3 right after differentiation occurs; and is further reduced to a significant low level of about 20% and 30%, respectively by day 7 after neural differentiation.

The markers provided herein are identified by microarray assays, which have been widely used for rapid gene expression monitoring and sequence analysis at the genomic level. The term "microarray" refers to an ordered spatial arrangement of immobilized biomolecular probes arrayed on a solid supporting substrate. Typically, such arrays are oligonucleotide arrays comprising a nucleotide sequence that is complementary to at least one sequence that may be or is expected to be present in a biological sample. For detail descriptions about microarray technology, please refer to "DNA Microarrays, Edited by M. Schena, In "The Practical Approach Series," Series Editor: B. D. Hames (2000) Oxford University Press Inc., New York".

Taking advantage of the advanced microarray technology, genes associated with stem cell differentiation were identified. In one embodiment, more than 100 genes were found to be down-regulated in the differentiated hESCs by RNA microarray analysis, with at least 2-folds lower expression level in differentiated cells than in control undifferentiated cells. Among these 100 genes, 2 genes (i.e., CBARA1 and LHX6) are novel and have never been disclosed or suggested in the prior art that they relate to stem cell differentiation. Polynucleotide sequences for the two genes, CBARA1 (SEQ ID NO 1) and LHX6 (SEQ ID NO 2) can be accessed by the access number NM_006077.2, and NM_014368.3, respectively; and the amino acid sequence for CBARA1 (SEQ ID NO 3) and LHX6 (SEQ ID NO 4) can be accessed by NP_006068.2 and NP_055183.2, respectively. The disclosure thus provides an isolated polynucleotide that relates to hESCs differentiation, the isolated polynucleotide comprises a nucleotide sequence that is at least 90%, 91%, 92%, 93%, 94%, 95%, 96%, 97%, 98% or 99% identical to any of SEQ ID NO 1 and 2. The isolated polynucleotide is at least 95%, 96%, 97%, 98% or 99% identical to any of SEQ ID NO 1 and 2.

Each of the identified polynucleotides encodes a polypeptide having an amino acid sequence that is at least 85%, 86%, 87%, 88%, 89%, 90%, 91%, 92%, 93%, 94%, 95%, 96%, 97%, 98% or 99% identical to any of SEQ ID NO 3 and 4 or a partial portion thereof. The polypeptide encoded by any of the polynucleotides described above is at least 95%, 96%, 97%, 98% or 99% identical to a polypeptide selected form any of SEQ ID NO 3 and 4, or a partial portion thereof.

The percentage of identity between a subject sequence and a reference standard can be determined by submitting both sequences to a computer analysis with any parameters affecting the outcome of the alignment set to the default position. Optimal alignment of sequences for aligning a comparison window are well known to those skilled in the art and may be conducted by tools such as the homology alignment algorithm, include, but are not limited to GAP, BESTFIT, FASTA, and TFASTA (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more nucleic acid sequences may be to a full-length nucleic acid sequence or a portion thereof, or to a longer nucleic acid sequence. In some instances, a subject sequence and the reference standard can exhibit the required percent identity without the introduction of gaps into one or both sequences. In many instances, the extent of identity will be evident without computer assistance. For example, one of ordinary skill in the art would readily be able to conclude that introducing an addition, deletion or substitution of a single amino acid residue into any of SEQ ID NO 3 and 4 would produce a mutant polypeptide that is at least 99% identical to its wild type polypeptide; and introducing an addition, deletion or substitution of two amino acid residues into any of SEQ ID NO 3 and 4 would produce a mutant polypeptide that is at least 98% identical to its wild type polypeptide; and so forth. Further, in many cases, polypeptides having deletion, substitution, insertion and/or addition of one or plural amino acids in the amino acid sequence of the desired protein have the same functional activity as that of desired protein. Genes encoding such polypeptides are also included in the present invention regardless of them being naturally occurring or artificial genes.

The detection, identification and/or discrimination of differentiated hESCs in a population of hESCs can be carried out by monitoring the expression of the identified genes. The disclosure thus provides a method of detecting, identifying and/or discriminating differentiated hESCs in a population of hESCs, comprising the steps of: obtaining a population of hESCs; measuring an expression level of one or more polynucleotides comprising a nucleotide sequence at least 90% identical to any of SEQ ID NO 1 and 2 in the hESCs; and determining whether the expression level of the one or more polynucleotides in the hESCs is at least two folds lower than the expression level of the one or more polynucleotides in the undifferentiated hESCs. A sub-population of hESCs that expresses the gene product at least 2-folds lower than that of a control population (i.e., undifferentiated cells) is thus categorized as being differentiated. The change of the expressed gene product may be determined by the change in a level of mRNA corresponding to said gene, or by the change in an expressed level of a protein encoded by said gene. In particular embodiments, the expression level of the one or more polynucleotides is determined by measuring the level of one or more polypeptides encoded by the one or more polynucleotides. The one or more polypeptides comprise amino acid sequences at least 80% identical to any of SEQ ID NO 3 and SEQ ID NO 4, or a partial portion thereof.

The disclosure further provides a method of enriching a population of undifferentiated hESCs, comprising the step of sorting hESCs by one or more cell markers selected from the group consisting of CBARA1 and LHX6; and selecting out the undifferentiated hESCs. In one example, the cell marker is one or more genes having a nucleotide sequence at least 90%, 91%, 92%, 93%, 94%, 95%, 96%, 97%, 98% or 99% identical to any of SEQ ID NO 1 and 2; or one or more proteins encoded by the one or more genes, and the one or more proteins comprise an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any of SEQ ID NO 3 and 4, or a partial portion thereof. Various techniques can be used herein to separate and enrich the desired differentiated and/or undifferentiated hESCs. Antibodies are particular useful for this purpose, the antibodies may detect the full molecule of CBARA1 and LHX6 or detect specific peptide sequences contained within CBARA1 and LHX6. The antibodies can be attached to a solid support to allow for crude separation. The separation techniques employed should maximize the retention viability of the fraction of cells to be collected. In one example, sorting is achieved by flow cytometry. It is to be noted that any method that can isolate and distinguish hESCs according to the levels of expression of CBARA1 and LHX6 may be used. Hence, the disclosure also provides a composition of enriched differentiated and/or undifferentiated hESCs, which are sorted by one or two cell markers selected from the group consisting of CBARA1 and LHX6. The expression level of gene products of any of CBARA1 and LHX6 is at least 2-folds lower in the enriched differentiated hESCs than the enriched undifferentiated hESCs.

As described above, significantly high levels of expression products of any of SEQ ID NO 1 and 2 indicate the presence of undifferentiated hESCs, and the levels decrease rapidly as the hESCs differentiated. A kit may thus be developed for discriminating differentiated hESCs from undifferentiated ones based on hybridization assay, western blot or enzyme-linked immunosorbent assay (ELISA) test. These assays are well known in the art. The kit may contain in separate containers a probe having a nucleotide sequence that is complementary to mRNA of a gene having a nucleotide sequence that is at least 90% identical to any of SEQ ID NO 1 and 2, or antibodies against a polypeptide or a portion thereof having an amino acid sequence at least 85% identical to any of SEQ ID NO 1 and 2; control formulations (either positive or negative); and instructions such as written direction, tape, VCR, CD-ROM and etc. for carrying out the assay that includes in the kit.

The stem cells in this study may be pluripotent. Stem cells herein include, but are not limited to, embryonic stem cells and induced pluripotent stem cells. Embryonic stem cells are pluripotent and are derived from embryos. In one example, the stem cells are human embryonic stem cells.

Reference will now be made in detail to the embodiments of the invention, examples of which are illustrated in the accompanying drawings. Wherever possible, the same reference numbers are used in the drawings and the description to refer to the same or like parts.

EXAMPLES

The following Examples are provided to illustrate certain aspects of the present invention and to aid those of skilled in the art in practicing this invention. These Examples are in no way to be considered to limit the scope of the invention in any manner.

Example 1

Culturing of hESCs and In Vitro Neural Differentiation hESC lines including H1, H9, TW1, TW5, HES03, and HES04 were maintained on culture plates coated with the extracellular matrix derived from human fibroblasts (Stematrix) in a medium conditioned with mouse embryonic fibroblasts (MEF) for 24 hours. The basal medium for hESC was DMEM/F12 (Invitrogen Corp.) supplemented with 15% knockout serum replacement (Invitrogen Corp.), 1 mmol/L l-glutamine (Invitrogen Corp.), 0.1 mmol/L β-mercaptoethanol (Invitrogen Corp.), 0.1 mmol/L MEM non-essential amino acids (Invitrogen Corp.), and 4 ng/ml recombinant human basic fibroblast growth factor (bFGF; Invitrogen Corp.). This methodology for hESC culture could provide pluripotent stem cells with a normal diploid karyotype. Cultured cells were passaged by dispase enzymatic dissociation when cells became subconfluent (i.e., about once a week).

Example 2

Identification of Cell Markers by Microarray Analysis

RNA Microarray Assay

Total RNAs of undifferentiated and differentiated hESC lines including H1, H9, TW1, TW5, HES03, and HES04 were isolated using TRIzol® reagent (Invitrogen, Carlsbad, Calif.) at 1, 3, 5 or 7 days following neural differentiation according to the manufacturer's protocol. The hybridization of microarray and the analysis of results were performed according to the manufacturer's protocol (Phalanx). Duplicate samples from two independent differentiations were analyzed. Differentially expressed genes were characterized by the following criteria: (1) there were present in undifferentiated samples, (2) they were decreased in at least one differentiation time-point, and (3) there was at least a 2-fold decreased in RNA levels.

In this study, differentially expressed genes that are highly expressed in undifferentiated hESCs and down-regulated (>2-fold) upon differentiation are selected as candidate markers. More than 100 genes were found down-regulated in differentiated hESCs, among which two genes (CBARA1, Gene Bank Access No: 10367; LHX6, Gene Bank Access No.: 26468), not previously associated with hESCs, were identified as candidate markers for subsequent analysis. FIG. 1 revealed CBARA1 and LHX6 gene expression profiles of hESCs at 1, 3, 5, or 7 days following differentiation. Both markers were expressed at high levels in undifferentiated hESCs, but were weakly expressed in neural differentiated cells at day 7 of differentiation. Following neural differentiation, CBARA1 and LHX6 were down regulated by 34% and 55%, respectively by day 3 and further reduced to 21% and 28%, respectively on day 7 (FIG. 1).

Western Blot Analysis

Figure 2:
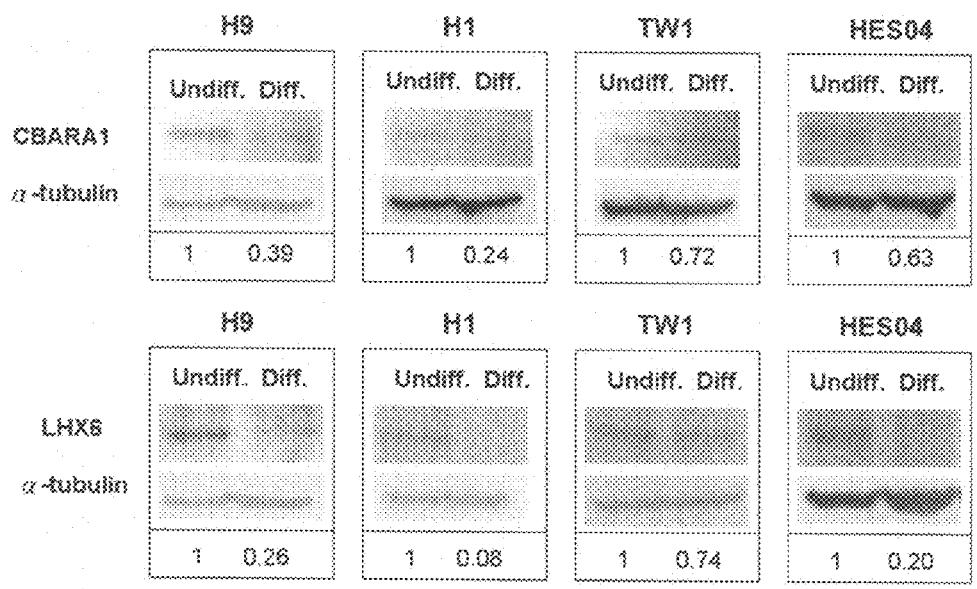
FIG. 2 illustrates expression level of CBARA1 and LHX6 in differentiated and undifferentiated cells measured at day 7 following neural differentiation.

Western blot analysis was performed to authenticate the results of the above microarray studies. Specifically, cells from H1, H9, TW1 and HES04 hESC lines were lysed by mixing the cells with Radio-Immunoprecipitation Assay (RIA) buffer (10 mM $Na_2HPO_4$, 150 mM NaCl, 1 mM EDTA, 1% NP40, 0.1% SDS, and 1% sodium deoxycholate) containing Proteinase Inhibitor Cocktail (Roche) and phosphatase inhibitors (Sigma). The protein amounts in the cell lysates were quantified by Bradford protein assay kit according to the provider's protocol. For Western blot assay, the prepared samples were electrophoresed on 12% SDS-polyacrylamide gel under reducing conditions. After electrophoresis, the proteins were transferred electrophoretically to PVDF membrane (Immobilon™-P) from Millipore. The membrane was blocked with 5% skim milk for 1 hour at room temperature to saturate non-specific protein background on the membrane. After the blocking process, the membrane was incubated overnight with primary antibodies of CBARA1 (1:1000) or LHX6 (1:500) at 4° C. Both antibodies were purchased from Abnova Corp. The membrane was washed 3 times with buffer for 5 min each, and then incubated with secondary antibodies for 1 hr at room temperature. The membrane was visualized with a super signal west chemiluminescent substrate kit (Pierce), and quantified by densitometer analysis using FluorChemSP software with α-tubulin as a reference. Results were illustrated in FIG. 2.

Consistent with the microarray data, CBARA1 and LHX6 were expressed in much higher levels in undifferentiated hESCs (FIG. 2) when compared with those in neural differentiated cells.

Example 3

Using CBARA1 as a Cell Marker to Discriminate Differentiated hESCs from Un-Differentiated hESCs To determine whether CBARA1 could serve as a cell marker for early detection of differentiated cells in spontaneously differentiated hESC culture, CBARA1 expression level in hESCs was measured by immunocytochemistry and temporal expression of CBARA1 and Oct4 at 1, 3, 5 or 7 days following differentiation were determined by flow cytometry.

Immunocytochemistry

Cells were fixed with 4% paraformaldehyde at 4° C. for 15 min. For Oct4 staining, the cells were permeabilized in 0.1% Triton-X100 (Sigma-Aldrich) in PBS for 10 min. Fixed cells were washed with PBS and blocked in PBS containing 5% goat serum (Vector) for 1 hr at 4° C., followed by incubating with primary antibodies in PBS containing 1% goat serum at 4° C. overnight. Primary antibodies used were: rabbit anti-Oct4 (1:200, Abcam) and mouse anti-CBARA1 (1:100, Abnova Corp.). Alexa Fluor 488 anti-mouse IgG and Alexa Fluor 594 anti-rabbit IgG (Invitrogen Corp.) at a dilution of 1:500 were used for single or double labeling. Results were illustrated in FIG. 3.

Figure 3:
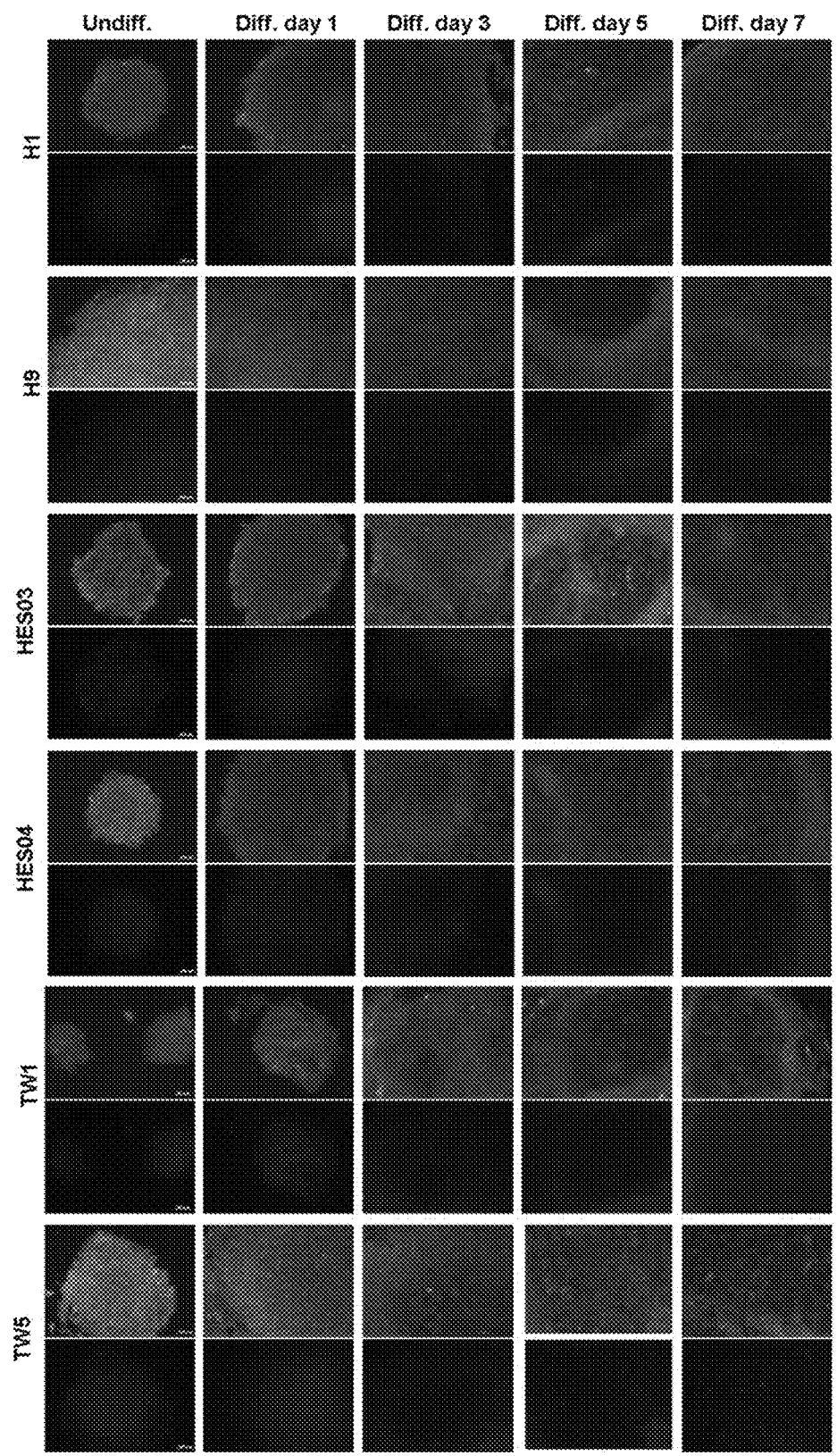
FIG. 3 is immunostaining depicting temporal expression of CBARA1 (green) and Dapi (blue) in various differentiated and undifferentiated stem cells during the differentiation time course.

It is evident from FIG. 3, CBARA1 was strongly expressed in undifferentiated hESCs and was down-regulated early following differentiation (FIG. 3). Majority of cells exhibited weak expression of CBARA1 at 7 days. CBARA1 staining was validated in various hESC lines including H1, H9, HES03, HES04, TW1 and TW5. Validation of LHX6 was not performed, because commercially available LHX6 antibodies were not suitable for immunocytochemistry.

Flow Cytometry

For analysis of expression of hESC markers, hESCs were dissociated into single cell suspension by treating with trypsin (1:5 dilution in PBS) for 10 min at 37° C. and fixed with 4% paraformaldehyde. The dissociated cells were re-suspended at a concentration of approximately $2 \times 10^5$ cells/ml in PBS and incubated with mouse anti-Oct4 (1:200, Millipore), mouse anti-CBARA1 (1:50, Abnova Corp.) and mouse anti-IgG antibody (1:1000, Serotec), respectively for 30 min at 4° C. After washing, the cells were incubated with Alexa 488-conjugated anti-mouse antibody for 30 min at 4° C. Cells were analyzed using FACSCalibur (BD Immunocytometry System) and Cell Quest software (BD Immunocytometry System). Results were illustrated in FIGS. 4 and 5.

Figure 4:
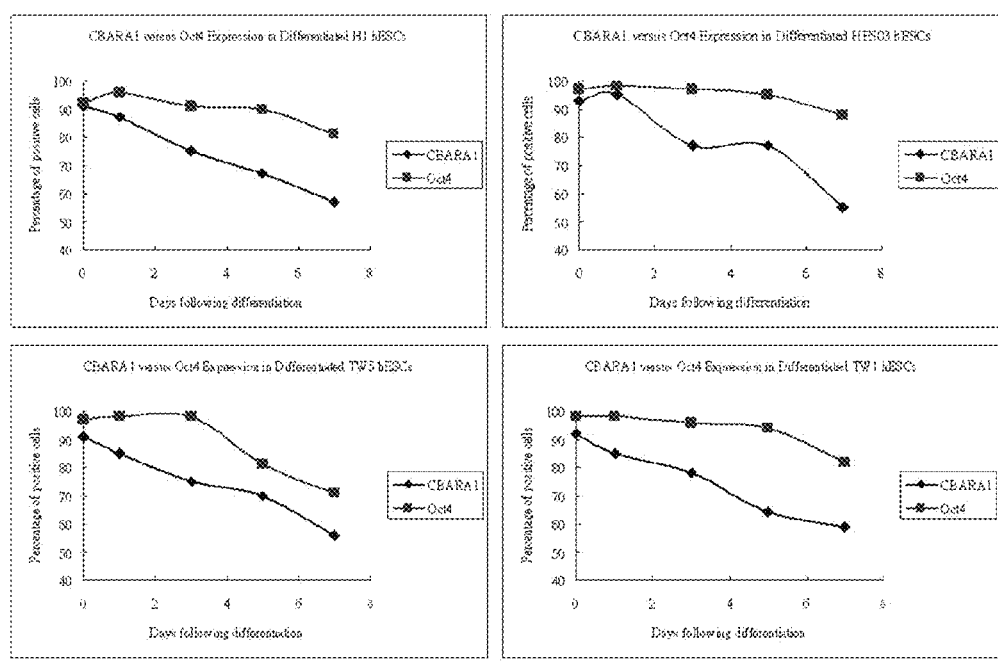
FIG. 4 illustrates identification of CBARA1-positive population versus Oct4-positive population in various hESC lines including H1, HES03, TW1, and TW5 lines, by flow cytometry following spontaneous differentiation of these lines.
Figure 5:
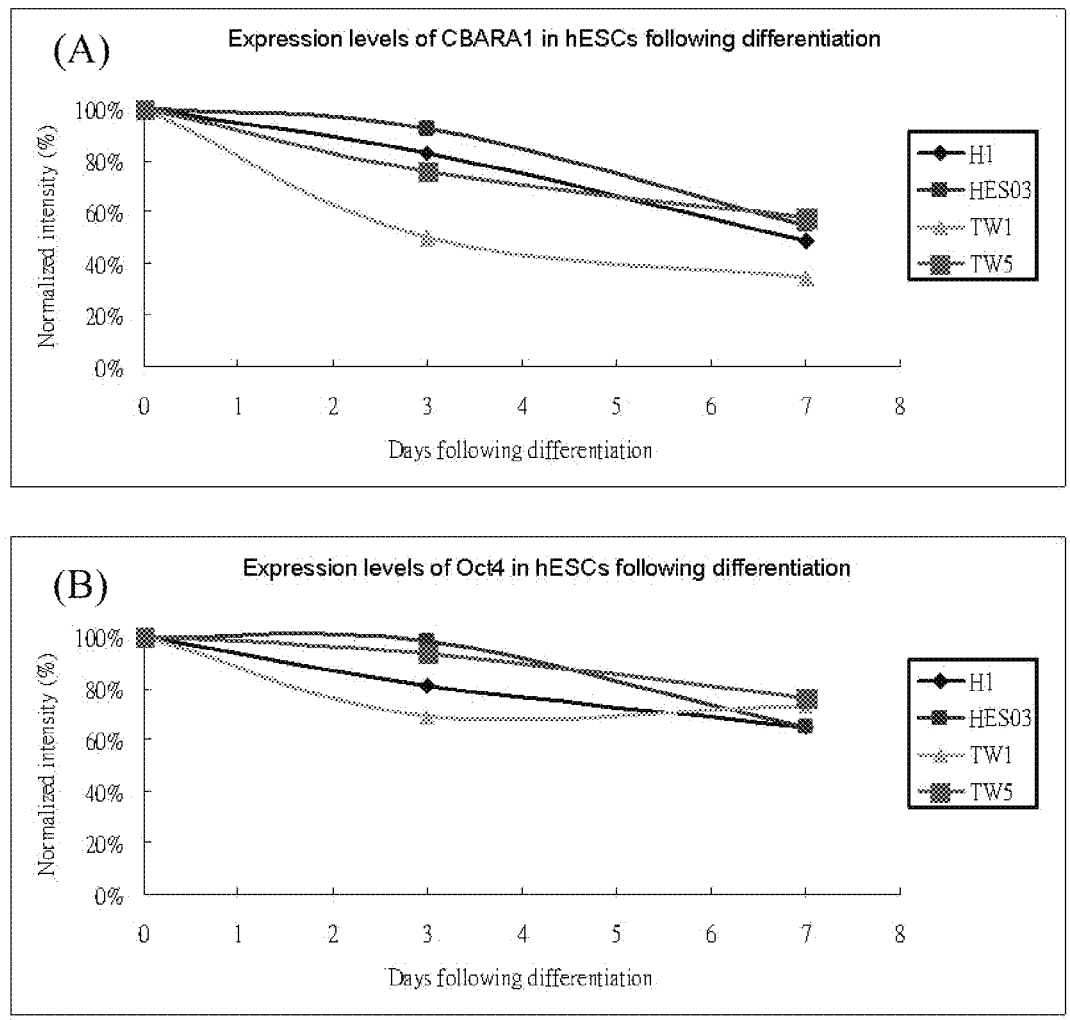
FIG. 5 illustrates the expression levels of (A) CBARA1 and (B) Oct4 in various hESC lines following spontaneous differentiation.

Prior to differentiation, over 90% of cells were positive for both CBARA1 and Oct4, which suggested that the majority of hESCs were undifferentiated. Following spontaneous differentiation, the percentage of CBARA1-positive cells rapidly reduced as compared to Oct4-positive cells in differentiated culture (FIG. 4). The percentage of CBARA1 positive cells declined to about 70-80% by day 3 and further reduced to a low level of about 50-60% by day 7 after differentiation. In contrast, the percentage of Oct4-positive cells remained relatively the same at a high level of over 90% at day 3 after differentiation and slowly dropped to a level of about 70-90% by day 7. Subsequent analysis of CBARA1- or Oct4-positive cells at day 0, 3 and 7, respectively indicated that the normalized relative intensity of CBARA1 expression was reduced to a greater extent in hESCs, as compared with Oct4 expression levels over the time-course of differentiation (FIG. 5). Overall, these results suggest that CBARA1 is a sensitive marker for early detection of hESC differentiation.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of discriminating differentiated human embryonic stem cell (hESC) population comprising:
   obtaining a population of hESCs;
   measuring an expression level of one or more polynucleotides comprising a nucleotide sequence at least 90% identical to any of SEQ ID NO 1 and SEQ ID NO 2 in the hESCs; and
   determining the expression level of the one or more polynucleotides in the population of hESCs,
   wherein those cells in the hESCs population having at least 2-fold lower expression level of said one or more polynucleotides discriminates differentiated hESC population.

2. The method of claim 1, wherein the one or more polynucleotides comprise a nucleotide sequence at least 95% identical to any of SEQ ID NO 1 and SEQ ID NO 2.

3. The method of claim 1, wherein the one or more polynucleotides comprise a nucleotide sequence at least 98% identical to any of SEQ ID NO 1 and SEQ ID NO 2.

4. The method of claim 1, wherein the expression level of the one or more polynucleotides is determined by measuring the level of one or more mRNAs encoding the one or more polynucleotides, and the one or more polypeptides comprise amino acid sequences at least 80% identical to any of SEQ ID NO: 3 and SEQ ID NO: 4.

5. The method of claim 1, wherein the expression level of the one or more polynucleotides is determined by measuring the level of one or more polypeptides encoded by the one or more polynucleotides following differentiation.

6. The method of claim 5, wherein the one or more polypeptides comprise amino acid sequences at least 85% identical to any of SEQ ID NO: 3 and SEQ ID NO: 4.

7. The method of claim 6, wherein the one or more polypeptides comprise amino acid sequences at least 90% identical to any of SEQ ID NO: 3 and SEQ ID NO: 4.

8. The method of claim 7, wherein the one or more polypeptides comprise amino acid sequences at least 95% identical to any of SEQ ID NO: 3 and SEQ ID NO: 4.

9. A method of enriching a population of undifferentiated hESCs comprising the steps of:
   obtaining a population of hESCs;
   sorting the population of hESCs by at least one cell markers of CBARA1 and LHX6; and
   separating from the population hESC those hESCs expressing at least 30% decrease of the at least one cell markers of CBARA1 and LHX6,
   thereby producing a population of hESCs enriched for expression of CBARA1 and LHX6.

10. The method of claim 9, wherein CBARA1 and LHX6 respectively comprises a polynucleotide comprising a nucleotide sequence at least 90% identical to SEQ ID NO 1 and SEQ ID NO 2, respectively.

11. The method of claim 10, wherein CBARA1 and LHX6 respectively comprises a polynucleotide comprising a nucleotide sequence at least 95% identical to SEQ ID NO 1 and SEQ ID NO 2, respectively.

12. The method of claim 11, wherein CBARA1 and LHX6 respectively comprises a polynucleotide comprising a nucleotide sequence at least 98% identical to SEQ ID NO 1 and SEQ ID NO 2, respectively.

13. The method of claim 10, wherein CBARA1 and LHX6 respectively encodes a polypeptide comprising an amino acid sequence at least 80% identical to SEQ ID NO: 3 and SEQ ID NO: 4, respectively.

14. The method of claim 13, wherein CBARA1 and LHX6 respectively encodes a polypeptide comprising an amino acid sequence at least 85% identical to SEQ ID NO: 3 and SEQ ID NO: 4, respectively.

15. The method of claim 14, wherein CBARA1 and LHX6 respectively encodes a polypeptide comprising an amino acid sequence at least 90% identical to SEQ ID NO: 3 and SEQ ID NO: 4, respectively.

16. The method of claim 15, wherein CBARA1 and LHX6 respectively encodes a polypeptide comprising an amino acid sequence at least 95% identical to SEQ ID NO: 3 and SEQ ID NO: 4, respectively.

* * * * *